United States Patent [19]  
Mita et al.

[11] 4,304,933
[45] Dec. 8, 1981

[54] PRODUCTION OF DL-SERINE

[75] Inventors: Ryuichi Mita, Kawasaki; Chojiro Higuchi, Kamakura; Toshio Kato, Kawasaki; Nobuyuki Kawashima; Akihiro Yamaguchi, both of Kamakura; Shosuke Nagai, Yokohama; Takao Takano, Fujisawa, all of Japan

[73] Assignee: Mitsui Toatsu Chemicals, Inc., Tokyo, Japan

[21] Appl. No.: 212,102

[22] Filed: Dec. 2, 1980

[30] Foreign Application Priority Data

Dec. 10, 1979 [JP] Japan ............................. 54/159250
Dec. 12, 1979 [JP] Japan ............................. 54/160350

[51] Int. Cl.³ .......................................... C07C 101/30
[52] U.S. Cl. .............................. 562/567; 260/239 AA
[58] Field of Search ........................................ 562/567

[56] References Cited
PUBLICATIONS

Berse, Con. J. Chem., 49, p. 2610–2611 (1971).
Gundermann et al., *Chem. Ber.*, vol. 93, pp. 1632–1633, 1634–1635, 1638–1641 (1960).
Kyburz, E., *Hev. Chim. Acta*, vol. 49, pp. 364–365 and 366–367, 359 and 368 (1966).

*Primary Examiner*—Natalie Trousof
*Assistant Examiner*—Michael L. Shippa
*Attorney, Agent, or Firm*—Fisher, Christen & Sabol

[57] ABSTRACT

Production of DL-serine by heating a strong acid type cation exchange resin having aziridine-2-carboxylic acid absorbed thereto. Specifically, an industrial process for producing DL-serine is provided which comprises treating an alpha-halogeno-beta-aminopropionitrile or its mineral acid salt in water or a water-containing organic solvent with an alkali or alkaline earth metal hydroxide to form an alkali or alkaline earth metal aziridine-2-carboxylate, treating the reaction mixture with a strong acid type cation exchange resin to cause adsorption of aziridine-2-carboxylic acid, and thereafter heating the cation-exchange resin.

8 Claims, No Drawings

PRODUCTION OF DL-SERINE

BACKGROUND OF THE INVENTION

1. Field of the Invention

This invention relates to a process for producing serine.

2. DESCRIPTION OF THE PRIOR ART

Serine is a kind of an alpha-amino acid. L-serine is used as a component of a parenteral solution, and D-serine is useful as a material for cycloserine, an antibiotic. Serine is also useful as a material for the production by an enzymatic process of L-tryptophan which is expected to gain future acceptance as a feed additive.

One conventional process for production of DL-serine from aziridine-2-carboxylic acid comprises heating in 15% sulfuric acid lithium aziridine-2-carboxylate synthesized by hydrolysis of ethyl aziridine-2-carboxylate in the presence of lithium hydroxide [K. D. Gundermann, Chem. Ber., 93, 1639 (1960)]. This process, however, requires the use of a large excess (about 12 moles) of sulfuric acid relative to the starting lithium aziridine-2-carboxylate. In order to separate the resulting serine from the reaction mixture after the reaction, the excess sulfuric acid should be neutralized with calcium hydroxide or barium hydroxide to precipitate it as calcium sulfate or barium sulfate, followed by separating the salt by filtration. The process steps, therefore, become complex and the reactor volume is large. If an anion having higher nucleophilic reactivity than water, such as a halogen ion, is present in the hydrolysis of aziridine-2-carboxylic acid in sulfuric acid, a compound having such an ion added thereto forms as a by-product to decrease the yield of DL-serine.

It is an object of this invention therefore to provide a process for producing DL-serine from aziridine-2-carboxylic acid or its alkali or alkaline earth metal salt which can be produced relatively easily.

The salt of aziridine-2-carboxylate can be easily obtained by heating an aqueous solution of an alpha-halogeno-beta-aminopropionitrile or its mineral acid salt, which can be easily produced by the reaction of an alpha, beta-dihalogenopropionitrile or an alpha-halogenoacrylonitrile with ammonia, together with an alkali or alkaline earth metal hydroxide.

SUMMARY OF THE INVENTION

In order to achieve the above object, the present inventors have made extensive investigations, and found that DL-serine can be produced with industrial advantage by causing aziridine-2-carboxylic acid to be adsorbed to a strong acid type cation exchange resin, and heating the ion exchange resin in the wet state, and that DL-serine can be industrially produced by treating an alpha-halogeno-beta-aminopropionitrile or its mineral acid salt in water or a water-containing organic solvent with an alkali or alkaline earth metal hydroxide to form an aziridine-2-carboxylic acid salt, charging the reaction mixture onto a strong acid type cation exchange resin without isolating the product therefrom, thereby to adsorb aziridine-2-carboxylic acid, washing the resin with water to remove a halogen ion, and heating the ion exchange resin.

DETAILED DESCRIPTION OF THE INVENTION

The process of this invention is a novel process not known heretofore, and has the advantage that in contrast to the conventional hydrolyzing method in sulfuric acid, the process is markedly simplified, and serine is obtained in a high yield based on the aziridine-2-carboxylic acid without substantially forming a by-product. Another advantage of the process of this invention is that serine formed by the reaction can be simply isolated by washing the heated ion exchange resin with aqueous ammonia to elute the serine, and concentrating the eluate to dryness or concentrating and crystallizing it.

When according to one embodiment of the process of this invention the process starts from the production of an alpha-halogeno-beta-aminopropionitrile or its mineral acid salt, a halogen ion formed as a by-product in the production of an aziridine-2-carboxylic acid salt can be easily removed. Hence, this brings about the advantage that serine can be obtained in a high yield based on the starting alpha-halogeno-beta-aminopropionitrile or its mineral acid salt without substantial formation of by-products.

The aziridine-2-carboxylic acid or its alkali or alkaline earth metal salt to be adsorbed to a strong acid type cation exchange resin can be produced by a known method which comprises treating an alkyl aziridine-2-carboxylate obtained by reaction between an alkyl alpha,beta-dibromopropionate and liquid ammonia, with an alkali or alkaline earth metal [K. D. Gundermann, Chem. Ber., 93, 1639 (1960), E. Kyburz, Helv. Chim. Acta., 49, 368 (1966)] or a similar method. The aziridine-2-carboxylate salt produced by such a known method need not be isolated before being put to use in the process of this invention, and it may be used in the form of an aqueous solution obtained after the hydrolysis of the alkyl aziridine-2-carboxylate. Such an aqueous solution may, for example, be an aqueous solution of sodium aziridine-2-carboxylate obtained by hydrolyzing isopropyl aziridine-2-carboxylate obtained from isopropyl alpha, beta-dibromopropionate and liquid ammonia with sodium hydroxide in a mixture of ethanol and water and distilling off the alcohol under reduced pressure, or an aqueous solution of a salt of aziridine-2-carboxylic acid with another alkali or alkaline earth metal which is obtained by a similar method.

The aziridine-2-carboxylic acid or its alkali or alkaline earth metal salt to be adsorbed to the strong acid type cation exchange resin in the process of this invention may also be produced by a novel method discovered by the present inventors which comprises treating an alpha-halogeno-beta-aminopropionitrile or its mineral acid salt with an alkali or alkaline earth metal hydroxide in water or a water-containing organic solvent.

Examples of the alpha-halogeno-beta-aminopropionitrile or its mineral acid used in this method include alpha-chloro-beta-aminopropionitrile, alpha-bromo-beta-aminopropionitrile, alpha-chloro-beta-aminopropionitrile hydrochloride, alpha-bromo-beta-aminopropionitrile hydrochloride, alpha-chloro-beta-aminopropionitrile sulfate and alpha-bromo-beta-aminopropionitrile sulfate. These alpha-halogen-beta-aminopropionitriles or their mineral acid salts can be produced in the following manner. A free alpha-halogeno-beta-aminopropionitrile is obtained by reacting an alpha,beta-dihalogenopropionitrile or alpha-halogenoacrylonitrile with ammonia in water or an organic solvent, optionally extracting the reaction product with a water-immiscible organic solvent, and distilling the reaction product under reduced pressure. Action of hydrogen chloride or sulfuric acid on the reaction product mixture or the extract gives an alpha-halogeno-beta-aminopropionitrile hydrochloride or sulfate. For example, an alpha-chloro-beta-aminopropionitrile hydrochloride can be isolated in a yield of more than 80% by adding alpha-chloroacrylonitrile dropwise at about 0° C. to a solution of ammonia gas in isopropanol, reacting them at this temperature for 2 to 4 hours, and then feeding a solution of hydrogen chloride in isopropanol into the reaction mixture.

The alkali or aklaline earth metal hydroxide used in this method is a hydroxide of an alkali metal such as lithium, sodium, potassium and rubidium, or a hydroxide of an alkaline earth metal such as beryllium, magnesium, calcium, strontium and barium. Specific examples are lithium hydroxide, sodium hydroxide, potassium hydroxide, beryllium hydroxide, magnesium hydroxide, calcium hydroxide and barium hydroxide.

The amount of the alkali or alkaline earth metal hydroxide is at least 2 equivalents based on the starting material when the starting material is a free alpha-halogeno-beta-aminopropionitrtile, and at least 3 equivalents based on the starting material when the starting material is an alpha-halogeno-beta-aminopropionitrile mineral acid salt. There is no specific upper limit to the amount of the hydroxide used, but it is not necessary to use it in great excess. Usually, up to 5 equivalents are sufficient.

The reaction is carried out in water or a water-containing organic solvent. In other words, the reaction is carried out in an aqueous solution or in a solution of a mixture of water and a water-miscible organic solvent. Examples of the water-miscible organic solvent include methanol, ethanol, n-propanol, isopropanol, tert-butanol, Cellosolve or methyl Cellosolve, acetone, dioxane, tetrahydrofuran, N,N-dimethyl formamide, N,N-diethyl formamide and dimethyl sulfoxide. When a mixture of water and an organic solvent is used, the ratio of water to the organic solvent may be chosen as desired. The amount of the solvent used is 3 to 200 times, preferably 5 to 100 times, the amount of the starting alpha-halogeno-beta-aminopropionitrile.

The reaction is carried out by dissolving the alpha-halogeno-beta-aminopropionitrile or its mineral acid salt in water, while stirring the solution adding the alkali or alkaline earth metal hydroxide in the form of an aqueous solution or as a solid, and continuing the stirring at 0° to 100° C. for 0.5 to 50 hours, preferably at 20° to 80° C. for 1 to 30 hours. The order of addition of the starting material and the alkali is not specially limited to the above-mentioned order. For example, the alpha-halogeno-beta-aminopropionitrile or its mineral acid salt may be added to an aqeuous solution or a suspension of the alkali or alkaline earth metal hydroxide. The end point of the reaction may be determined by thin-layer chromatography, etc.

In practicing the process of this invention, an aqueous solution of aziridine-2-carboxylic acid or an aqueous solution containing its alkali or alkaline earth metal salt (for example, an aqueous solution containing an alkali or alkaline earth metal aziridine-2-carboxylate obtained by treating an alpha-halogeno-beta-aminopropionitrile with an alkali or alkaline earth metal hydroxide) is charged onto a strong acid type cation exchange resins, and deionized water is then passed through the resin to adsorb aziridine-2-carboxylic acid to the ion exchange resin. The aqueous solution of the aziridine-2-carboxylic acid or its metal salt may contain a water-miscible organic solvent such as methanol and ethanol.

The halogen ion of a metal halide formed as a by-product in the formation of aziridine-2-carboxylic acid from the alpha-halogeno-beta-aminopropionitrile is removed preferably by passing deionized water. When the halogen ion remains, the yield of DL-serine tends to decrease. Subsequently, the ion exchange resin having adsorbed thereto aziridine-2-carboxylic acid is heated in the wet state to form DL-serine in the adsorbed state.

The strong acid type cation exchange resin may be of any form such as H, Na or $NH_4$. Preferably it is in H form. Any kind of ion exchange resins such as a gel, porous or macroporous type can be used. The type of the resin is not limited so long as it is a strong acid type cation exchange resin. Two or more different types of strong acid type cation exchange resins may be used in combination. The amount of the ion exchange resin used is at least 1 equivalent, preferably at least 1.2 equivalents, as an ion exchange capacity in the wet state based on the total amount of the aziridine-2-carboxylic acid and the alkali or alkaline earth metal ion present in the aqueous solution. For example, when 1 mole of sodium aziridine-2-carboxylate is used as a starting material and a strong acid type cation exchange resin having a total exchange capacity of 2.0 meq./ml is used, the amount of the resin used is at least 1 liter, preferably at least 1.2 liters. When aziridine-2-carboxylic acid is produced by treating 1 mole of alphachloro-beta-aminopropionitrile hydrochloride in water with 3 moles of sodium hydroxide, and a strong acid type cation exchange resin having a total exchange capacity of 2.2 meq./ml is used, the amount of the resin is at least 2.3 liters, preferably at least 2.7 liters. If the amount of the resin used is smaller than the specified limit, aziridine-2-carboxylic acid may leak out at the time of adsorption. The amount of the ion exchange resin used may be decreased by using an aqueous solution obtained by concentrating the reaction mixture containing the aziridine-2-carboxylate salt and removing the precipitated metal halide by filtration.

Adsorption of aziridine-2-carboxylic acid to the strong acid type cation exchange resin in the process of this invention may be performed usually by passing an aqueous solution of aziridine-2-carboxylic acid through a column packed with the ion exchange resin, or adding dilute hydrochloric acid, dilute sulfuric acid, etc. to the aqueous solution and thus passing the aqueous solution in a neutral or weakly acidic condition; and thereafter passing deionized water through the column. The concentration of aziridine-2-carboxylic acid in the aqueous solution of aziridine-2-carboxylic acid is not particularly limited, but preferably it is up to 15% by weight.

When the aziridine-2-carboxylic acid produced from an alpha-halogeno-beta-aminopropionitrile or its mineral acid salt is used, it may be caused to be adsorbed to the strong acid type cation exchange resin in the same way as above.

When a water-miscible organic solvent is used in the reaction, the solution to be adsorbed to the cation exchange resin may contain the organic solvent used, but preferably it is distilled off prior to adsorption. After passing the aqueous solution of aziridine-2-carboxylic acid through the ion exchange resin, the resin column is washed with water until no halogen ion is detected from the washing. When a halogen ion is present in the ion exchange resin column having adsorbed thereto aziridine-2-carboxylic acid, an alpha-halogeno-beta-alanine or beta-halogenoalanine is formed as a by-product in the subsequent heating of the ion exchange resin, and the yield of the desired serine decreases.

According to the process of this invention, the strong acid type cation exchange resin having adsorbed thereto aziridine-2-carboxylic acid and being free from a halogen ion is heated in the wet state, namely in the presence of water. There is no specific limitation on the method of heating the ion exchange resin. For example, heated water may be continuously passed through the ion exchange resin column, or the column packed with the ion exchange resin may be heated externally. Alternatively, the ion exchange resin is transferred to a separate heating vessel and heated with stirring.

The heating is effected at 40° to 120° C. for 1 to 100 hours, preferably at 50° to 100° C. for 2 to 50 hours. The reaction proceeds at a temperature of not more than 40° C., for example at room temperature, but a very long period of time is required for completion of the reaction.

DL-serine formed by heating the ion exchange resin having adsorbed thereto aziridine-2-carboxylic acid exists in the adsorbed state. To isolate serine, it is eluted from the ion exchange resin, for example by using aqueous ammonia, and the eluate is concentrated to dryness. Or the eluate is concentrated to a concentration above the solubility of serine, and then serine is crystallized.

The following examples illustrate the present invention.

REFERENTIAL EXAMPLE 1

Synthesis of lithium aziridine-2-carboxylate:

100 g of ethyl-alpha-chloro-beta-aminopropionate was dissolved in 1 liter of dehydrated ethanol, and 200 g of triethanolamine was added. They were reacted at 60° to 70° C. for 5 hours with stirring. Triethanolamine hydrochloride which precipitated was separated by filtration, and washed with a small amount of ethanol. The filtrate and the washing were combined, and 550 ml of a 1 N aqueous solution of lithium hydroxide was added with cooling. The mixture was added with gradually with cooling, and allowed to stand for 24 hours in a refrigerator. Then, the reaction mixture was concentrated to dryness under reduced pressure, and 200 ml of benzene was added to the residue (syrupy material), and water was completely removed by azeotropic distillation. Subsequently, 400 ml of hot ethanol was added, and the mixture was cooled to form a precipitate. The crystals were fully precipitated by adding 800 ml of ether. The precipitate was separated by filtration, and washed with ether to afford 11.2 g of lithium aziridine-2-carboxylate having a melting point of 261°–267° C. (decomp.).

REFERENTIAL EXAMPLE 2

Synthesis of sodium aziridine-2-carboxylate:

20 g of isopropyl aziridine-2-carboxylate synthesized from isopropyl alpha,beta-dibromopropionate and liquid ammonia was dissolved in 600 ml of dehydrated ether. With stirring, a solution of 4.0 g of sodium in 60 ml of ethanol was gradually added dropwise to the solution while cooling it. Ether (550 ml) was further added. Then, 3.2 g of water was added dropwise, and the mixture was allowed to stand at room temperature for 3 hours. The precipitated needle-like crystals were separated by filtration, and dried under vacuum to afford 14.2 g of sodium aziridine-2-carboxylate having a melting point of 153° to 156° C.

EXAMPLE 1

9.2 g of the lithium aziridine-2-carboxylate synthesized in Referential Example 1 was dissolved in 200 ml of water, and with cooling, it was neutralized with 5% sulfuric acid. The resulting aqueous solution was passed through a column packed with 280 ml of a strong acid type cation exchange resin, Lewatit S-100 (H-form) (a trademark for a product of Bayer AG). The column was washed with 300 ml of distilled water to adsorb aziridine-2-carboxylic acid. Then, the ion exchange resin was heated by circulating hot water at 90° to 95° C. for 6 hours. After the reaction, the ion exchange resin column was cooled, and eluted with 500 ml of 3 N aqueous ammonia and 500 ml of distilled water. The eluate was concentrated to dryness to afford 10.5 g of DL-serine having a purity of 93.5%.

The yield of DL-serine was 93.5% based on the lithium aziridine-2-carboxylate.

EXAMPLE 2

Example 1 was repeated except that 10.9 g of sodium aziridine-2-carboxylate synthesized in Referential Example 2 was used instead of the lithium aziridine-2-carboxylate, and 400 ml of Lewatit SP-120 (H-form) (a trademark for a product of Bayer AG) was used instead of Lewatit S-100. There was obtained 10.3 g of DL-serine having a purity of 92.8%.

EXAMPLE 3

In the procedure of Example 1, the ion exchange resin having adsorbed thereto aziridine-2-carboxylic acid was transferred to a 500 ml flask, and reacted at 90° to 95° C. for 6 hours in the flask. Then, the ion exchange resin was eluted with aqueous ammonia and water in the same way as in Example 1 to afford 10.5 g of DL-serine having a purity of 93.2%.

EXAMPLE 4

Example 1 was repeated except that the aqueous solution of lithium arizidine-2-carboxylate was adsorbed to the ion exchange resin while it was maintained alkaline. There was obtained 10.4 g of DL-serine having a purity of 92.1%.

EXAMPLE 5

14.1 g of alpha-chloro-beta-aminopropionitrile hydrochloride was dissolved in 160 g of water, and with stirring, an aqueous solution of 12.8 g of sodium hydroxide in 90 g of water was added dropwise gradually. Then, the reaction mixture was heated to 60° C., and reacted at 60° to 65° C. for 4 hours. The reaction solution was cooled, neutralized with a 5% aqueous solution of sulfuric acid, and passed through a column packed with 600 ml of a strong acid type cation exchange resin, Lewatit S-100 (H-form). Distilled water was passed through the column until no chlorine ion was detected from the effluent. Hot water heated at 90° to 95° C. was circulated for 6 hours through the ion exchange resin column having adsorbed thereto aziridine-2-carboxylic acid. After the reaction, the ion exchange resin was cooled, and eluted with 1 liter of 3 N aqueous ammonia and 1 liter of distilled water. The eluate was concentrated to dryness to afford 10.2 g of DL-serine having a purity of 90%. The yield of DL-serine was 87.4% based on the alpha-chloro-beta-aminopropionitrile hydrochloride. The proportion of by-product iso-serine was 4% based on the alpha-chloro-beta-aminopropionitrile.

Sodium aziridine-2-carboxylate formed in an intermediate stage was analyzed by high-speed liquid chromatography. The proportion of this intermediate formed was 95.8% based on the alpha-chloro-beta-aminopropionitrile hydrochloride.

EXAMPLES 6 to 9

Example 5 was repeated except that each of the strong acid type cation exchange resins shown in Table 1 below was used instead of Lewatit S-100. The results are shown in Table 1.

TABLE 1

| Example | Strong acid type cation exchange resin (*) | Yield of serine based on the alpha-chloro-beta-aminopropionitrile hydrochloride (%) |
|---|---|---|
| 6 | Lewatit SP-120 | 86.7 |
| 7 | Diaion SK-1B | 86.9 |
| 8 | Diaion PK-228 | 87.8 |
| 9 | Amberlite IR-121 | 85.4 |

(*) All resins were in H-form.

EXAMPLE 10

Example 5 was repeated except that 15.4 g of alpha-chloro-beta-aminopropionitrile sulfate was used instead of the alpha-chloro-beta-aminopropionitrile hydrochloride, and 22.4 g of potassium hydroxide was used instead of sodium hydroxide. There was obtained 10.3 g of DL-serine having a purity of 90.3%. The yield of the product was 88.6% based on the alphachloro-beta-aminopropionitrile sulfate.

EXAMPLE 11

10.5 g of free alpha-chloro-beta-aminopropionitrile was added to 100 g of water, and an aqueous solution of 8.8 g of lithium hydroxide in 80 g of water was added dropwise. They were reacted at room temperature for 24 hours.

The resulting reaction mixture was passed through a column packed with 400 ml of a strongly acid type cation exchange resin Lewatit S-100 (H-form). The column was washed with distilled water until no chlorine ion was detected in the effluent. Then, the ion exchange resin was transferred to a 500 ml flask, and with stirring, reacted at 50° to 60° C. for 20 hours. After the reaction, the ion exchange resin was packed in a dropping funnel, and eluted with 800 ml of 3 N aqueous ammonia and 800 ml of distilled water. The eluate was concentrated to dryness to afford 10.2 g of DL-serine having a purity of 92%. The yield of the product was 89.4% based on the alpha-chloro-beta-aminopropionitrile.

EXAMPLE 12

14.1 g of alpha-chloro-beta-aminopropionitrile hydrochloride was added to 160 g of water, and with stirring, 12 g of calcium hydroxide was gradually added to the solution. The mixture was heated to 60° C. and then reacted for 8 hours at 60° to 65° C. After the reaction, the excess of calcium hydroxide was removed by filtration. The filtrate was caused to be adsorbed to a strong acid type cation exchange resin Lewatit S-100 (H-form) in the same way as in Example 5, and a chlorine ion was removed. Subsequently, hot water at 80° to 90° C. was circulated through the column for 10 hours. The column was then eluted with 1 liter of 3 N aqueous ammonia and 1 liter of distilled water. The eluate was concentrated to dryness under reduced pressure to afford 10.4 g of DL-serine having a purity of 90.5%. The yield of the product was 89.6% based on the alpha-chloro-beta-aminopropionitrile hydrochloride.

What is claimed is:

1. A process for producing DL-serine, which comprises causing aziridine-2-carboxylic acid to be adsorbed to a strong acid type cation exchange resin, and thereafter heating the cation exchange resin in the wet state.

2. The process of claim 1 wherein the heating is carried out at a temperature of 40° to 120° C.

3. A process for producing DL-serine, which comprises passing an aqueous solution or a water-containing organic solvent solution containing aziridine-2-carboxylic acid or its alkali or alkaline earth metal salt through a strong acid type cation exchange resin, and thereafter heating the cation exchange resin in the wet state.

4. The process of claim 3 wherein the aqueous solution or water-containing organic solvent solution of aziridine-2-carboxylic acid or its alkali or alkaline earth metal salt is a reaction mixture obtained by treating an alphahalogen-beta-aminopropionitrile or its mineral acid salt with an alkali or alkaline earth metal hydroxide in water or a water-containing organic solvent.

5. The process of claim 3 wherein the heating is carried out at a temperature of 40° to 120° C.

6. The process of claim 3 or 4 wherein said water-containing organic solvent is a mixture of water with at least one water-miscible organic solvent selected from methanol, ethanol, n-propanol, isopropanol, tert.-butanol, Cellosolve, methyl Cellosolve, acetone, dioxane, tetrahydrofuran, N,N-dimethyl formamide and diemthyl sulfoxide.

7. A process for producing DL-serine, which comprises passing an aqueous solution or a water-containing organic solvent solution containing aziridine-2-carboxylic acid or its salt through a strong acid type cation exchange resin, then heating the cation exchange resin having aziridine-2-carboxylic acid adsorbed thereto in the wet state at 40° to 120° C., and then eluting adsorbed DL-serine from said resin.

8. A process as claimed in claim 3 or 7 wherein after said solution is passed through said cation exchange resin, deionized water is passed through the resin prior to said heating.

* * * * *